(12) United States Patent
Prussin

(10) Patent No.: US 7,078,919 B2
(45) Date of Patent: Jul. 18, 2006

(54) IN SITU DETERMINATION OF RESISTIVITY, MOBILITY AND DOPANT CONCENTRATION PROFILES

(76) Inventor: Simon A. Prussin, 1513 Pandora Ave., Los Angeles, CA (US) 90024

( * ) Notice: Subject to any disclaimer, the term of this patent is extended or adjusted under 35 U.S.C. 154(b) by 0 days.

(21) Appl. No.: 10/927,945

(22) Filed: Aug. 26, 2004

(65) Prior Publication Data
US 2005/0052191 A1 Mar. 10, 2005

Related U.S. Application Data

(60) Provisional application No. 60/588,255, filed on Jul. 14, 2004, provisional application No. 60/498,614, filed on Aug. 27, 2003.

(51) Int. Cl.
*G01R 31/26* (2006.01)
*G01N 27/00* (2006.01)
(52) U.S. Cl. ............... 324/719; 324/71.5; 438/17; 438/18
(58) Field of Classification Search ............... 324/719, 324/691, 71.5
See application file for complete search history.

(56) References Cited

U.S. PATENT DOCUMENTS

| | | | |
|---|---|---|---|
| 3,554,891 A | | 1/1971 | Duffy et al. ............... 204/400 |
| 3,660,250 A | * | 5/1972 | Duffy et al. ............... 205/790.5 |
| 4,303,482 A | | 12/1981 | Buhne et al. ............... 205/646 |
| 5,217,907 A | * | 6/1993 | Bulucea et al. ............... 438/17 |
| 6,087,189 A | * | 7/2000 | Huang ............... 438/10 |
| 2005/0124085 A1 | * | 6/2005 | Andoh et al. ............... 438/17 |

FOREIGN PATENT DOCUMENTS

GB 2 281 402 A 3/1995 ............... 324/719

OTHER PUBLICATIONS

L.J. van der Pauw, "A Method Of Measuring Specific Resistivity And Hall Effect Of Discs Of Arbitrary Shape", Philips Res. Repts. 13, pp. 1-9, 1958.

Eileen Tannenbaum, "Detailed Analysis Of Thin Phosphorus-Diffused Layers In p-Type Silicon", Solid Sate Electronics, vol. 2, pp. 123-132, 1961.

R. Galloni et al., "Fully Automatic Apparatus For The Determination Of Doping Profiles In Si By Electrical Measurements And Anodic Stripping", Rev. Sci. Instrum., vol. 54, No. 3, pp. 369-373, Mar. 1983.

(Continued)

*Primary Examiner*—Anjan Deb
(74) *Attorney, Agent, or Firm*—Fish & Richardson P.C.

(57) ABSTRACT

The present invention provides techniques for an in-situ measurement of resistivity profiles and dopant concentration distributions in semiconductor structures, such as shallow junctions. A substrate with a resistor test structure having a conduction circuit may be placed at a measurement station, surface layers may be successively removed from the conduction circuit at the measurement station, a sheet resistance of the conduction circuit may be measured at the measurement station after the removal of each surface layer to generate a plurality of sheet resistance measurements, and the resistivity profile may be calculated from the plurality of sheet resistance measurements.

43 Claims, 7 Drawing Sheets

OTHER PUBLICATIONS

A. Bartels et al., "*A Procedure For Temperature-Dependent, Differential Van Der Pauw Measurements*", Rev. Sci. Instrum., vol. 66, No. 8, pp. 4271-4276, Aug. 1995.

G. Queirolo, et al., "*Incremental sheet resistance and spreading resistance: A comparison*", J. Vac. Sci. Technol. B., vol. 10, No. 1, pp. 408-412, Jan./Feb. 1992.

Susan B. Felch, et al., "*A Comparison of Three Techniques for Profiling Ultrashallow $p^+$-n Junctions*", Solid State Technology, vol. 36, No. 1, pp. 45-51, Jan. 1993.

Min-Soo Kim, et al., "*In-situ Monitoring of Anodic Oxidation of p-type Si(100) by Electrochemical Impedance Techniques in Nonaqueous and Aqueous Solutions*", Bull. Korean Chem. Soc., vol. 20, No. 9, pp. 1049-1055, Sep. 1999.

Yoshio Kikuchi, et al., "*Quantitative Ultra Shallow Dopant Profile Measurement By Scanning Capacitance Microscope*", Fujitsu Sci. Tech. J., vol. 38, No. 1, pp. 75-81, Jun. 2002.

Joseph Plunkett et al., "A computer algorithm for accurate and repeatable profile analysis using anodization and stripping of silicon", Sol. St. Electr., vol. 20, p. 447-453 (1977).

Ryosaku Komatsu et al., "Novel Automatic measuring system for resistivity profiles in silicon wafers", Jap. J. of Appl. Phys., vol. 9, p. 169-173 (1980).

N.D. Young and M.J. Hight, "Automatic Hall effect profiler for electrical characterization", Electronic Letters, vol. 21, p. 1044-1046 (1985).

L.Bours and D.Tsoukalas, "Determination of doping and mobility profiles by automatic electrical measurement and anodic stripping", J. Phys. E. Sci. Instruments, vol. 20, p. 541-544 (1987).

S.R. Blight et al., "Automated Hall profiling system for the characterization of semiconductors at room and liquid nitrogen temperature", J. Phys. E. Sci. Instrum., vol. 21, p. 470-479 (1988).

T. Alzanki, et al., "Differential Hall effect profiling of ultrashallow junctions in Sb implanted silicon", Appl. Phys. Lett., vol. 85, No. 11, Sep. 13, 2004, p. 1979-1980.

S.R. Blight et al., "Automated Hall profiling system for the characterization of semiconductors at room and liquid nitrogen temperature", J. Phys. E. Sci. Instrum., vol. 21, p. 470-479 (1988).

L. Bouro and D. Tsoukalas, "Determination of doping and mobility profiles by automatic electrical measurement and anodic stripping", J. Phys. E. Sci. Instruments, vol. 20, p. 541-544 (1987).

Ryosaku Komatsu et al., "Novel Automatic measuring system for resistivity profiles in silicon wafers", Jap. J. of Appl. Phys., vol. 9, p. 169-173 (1980).

Joseph Plunkett et al., "A computer algorithm for accurate and repeatable profile analysis using anodization and stripping of silicon", sol. St. Electr., vol. 20, p. 447-453 (1977).

N.D. Young and M.J. Hight, "Automatic Hall effect profiler for electrical characterization", Electronic Letters, vol. 21, No. 22, p. 1044-4046 (1985).

* cited by examiner

IN SITU DETERMINATION OF RESISTIVITY, MOBILITY AND DOPANT CONCENTRATION PROFILES

CROSS-REFERENCE TO RELATED APPLICATIONS

This application is a claims priority to U.S. Provisional Application Ser. No. 60/498,614, filed on Aug. 27, 2003, and to U.S. Provisional Application Ser. No. 60/588,255, filed Jul. 14, 2004.

BACKGROUND

This invention relates to characterizing semiconductor structures.

Shortly after the commercial development of the transistor and other structures built on semiconductor substrates, a four-point probe was introduced to measure the sheet resistance of doped semiconductor layers. (See for example, L. B. Valdes, Proc. IRE, Volume 42, 1954, or in A.S.T.M. Standard F374, Annual Book of A.S.T.M. Standards Vol. 10.05.) To measure dopant concentration as a function of depth in a substrate, layers were successively removed from the substrate by abrasive lapping or chemical etching. After removing each layer at a processing station, the substrate was transferred to a measurement station to measure the sheet resistance. As layers of known thickness are removed, the sheet resistance changes. From these changes, a resistivity profile can be calculated, and converted into a dopant concentration distribution based on an assumption of mobility values which provide a relationship between resistivity and dopant concentration.

Layers can also be removed from a silicon substrate by anodic oxidation that allows removing layers parallel to the surface, as reported by Eileen Tannenbaum of Bell Telephone Labs (Solid-State Electronics Vol. 2, 1961). Tannenbaum's technique includes growing an anodic oxide layer, stripping off the oxide layer with hydrofluoric acid to expose the bare silicon, and measuring the sheet resistance on this fresh bare surface with a four-point probe. Tannenbaum analyzed junction depths that were several microns deep, and each removed layer had a thickness of about 400 angstroms. Thus a single analysis required about fifty or more removing steps, and each step took about thirty minutes. Tannenbaum notes that when anodization has proceeded to within 2000 angstroms of the junction, where the sheet resistance is about 1000 ohm/square, the four-point probe measurements become imprecise. Shallow junctions that are less than 300 angstroms deep typically cannot be evaluated by Tannenbaum's technique.

In 1970, the technique of Hall effect measurement, described in detail in ASTM standard F76, Annual Book of ASTM Standards, vol. 10.05, was combined with the Tannenbaum anodic oxidation stripping technique (N. G. E. Johansson, J. W. Mayer, and D. J. Marsh, Solid-State Electronics vol. 13, 1970). A van der Pauw test resistor was etched out on the surface of a blanket implanted silicon wafer. The test station was a Hall-effect measurement apparatus which measured the sheet resistance under three conditions: with a positive magnetic field, an equal negative magnetic field and without any magnetic field. These measurements permit obtaining the resistivity profile and the mobility profile, and thus the dopant concentration distribution. However, this differential Hall effect (DHE) technique was subject to the time and labor limitations of the Tannebaum anodic oxidation stripping technique.

One attempt to automate the Hall effect measurement is described in R. Galloni and A. Sardo, Rev. Sci. Instrum., vol. 54, 1983. In this technique, a cloverleaf pattern is etched on a square of silicon that is mounted on a fiber-glass board holder and lowered into an anodizing pot where an oxide of predetermined thickness is grown. This specimen is raised from the anodizing pot and lowered successively into three additional pots, where it is washed, the anodic oxide is stripped with an HF solution, and the specimen is rinsed, respectively. After drying, the specimen is moved to an area where electrical measurements are made and the process is repeated. The authors mention a time span of three hours for the completion of their test.

Another technique, spreading resistance analysis (SRA), introduced by R. G. Mazur and D. H. Dickey, J. Electrochem. Society Vol. 113, page 255, 1966), uses a small piece of silicon that is angle-lapped, and its resistance is measured along the beveled surface. Because an entire profile can be evaluated in about thirty minutes using SRA, it became the standard method for generating resistivity profiles, as described in detail in A.S.T.M. standard F672 in the Annual Book Of ASTM Standards Vol. 10.05. SRA is typically not used for junctions having a depth of about 300 angstroms or less.

During the 1980's, secondary ion spectroscopy (SIMS) was adapted for dopant profile evaluation. This technique evaluates the dopant concentration distribution directly by sputter depth probing of a small piece of silicon that is broken out of the wafer and placed in the SIMS chamber. This technology requires a high cost equipment and highly trained operators. Thus these tests are carried out primarily by a small number of dedicated laboratories.

Other techniques for resisitivity profiling have also been proposed. These proposed techniques include scanning capacitance microscopy, nano capacitance-voltage method, scanning tunneling microscopy or the carrier illumination technique.

SUMMARY

The present invention provides techniques for an in-situ measurement of resistivity and/or dopant concentration profiles in semiconductor structures, such as shallow junctions.

The invention can make use of one or more of the following phenomena:
1. The thickness of anodic oxide formed is proportional to the forming voltage developed so that measurement of forming voltage permits accurate determination of the oxide thickness.
2. The growth of an anodic oxide film effectively removes a calculable thickness of doped silicon from the resistor circuit.
3. The thickness of silicon consumed is linearly related to the thickness of oxide formed.
4. The anodic oxide formed acts as an insulator, electrically isolating the silicon resistor from the electrolyte.
5. The use of a van der Pauw resistor permits the calculation of the sheet resistance to be independent of the resistor dimensions.
6. The use of the cross design of a van der Pauw resistor permits the sheet resistance measurement to be made over a very small area, the area at the junction of the four resistor arms.
7. The use of a liquid-containing electrode fixture permits us to anodically oxidize a doped silicon surface over a very small area.

8. The use of permanent magnets permits the introduction of high magnetic fields from the underside of the test specimen.

Equipment which incorporates these features permits us to effectively carry out a series of sheet resistance measurements (e.g., conventional sheet resistance or Hall sheet resistance) on a doped silicon surface from which thin incremental layers are sequentially removed. The incremental increase in sheet resistance (conventional and Hall sheet coefficient) enables the calculation, in a direct and simple manner, of the resistivity profile, the mobility profile, and the concentration distribution. A simplified technique which omits the measurement carried out under a magnetic field enables the calculation of the resistivity profile, which is often the only information desired.

The present techniques can be used for laboratory evaluations of shallow junction structures. In this case the test structure can be built on a small piece of a silicon wafer and solder contacts may be used. Or the techniques can be implemented as part of the production process for process control. In this case the measurements are made on a small test structure located on a production wafer using a probe station.

This invention is particularly adapted for directly measuring the resistivity and dopant concentration profiles of ultra-shallow junctions down to atomic dimensions. The sheet resistances measured with anodic oxide growth corresponding to a forming voltage increment of 2 Volts are measured at silicon depth increments of 4.4 angstroms (for comparison the width of an atomic layer of silicon is 2.71 angstroms). The measurements described by the invention require only a small area of the silicon surface and can be carried out on the test area of a large production wafer without damaging the wafer. Thus this permits this invention to be used for process monitoring in the production process.

In one aspect, the invention is directed to a method of determining the resistivity profile in a pn structure or in the silicon surface layer on a SOI (silicon on insulator) structure. The method includes placing a substrate with a resistor test structure having a conduction circuit on said pn or SOI structure at a measurement station, successively removing surface layers from the conduction circuit at the measurement station, measuring a sheet resistance of the conduction circuit at the measurement station after the removal of each surface layer to generate a plurality of sheet resistance measurements, and calculating the resistivity profile from the plurality of sheet resistance measurements.

In another aspect, the invention is directed to a method of characterizing a semiconductor layer. The method includes processing a production integrated circuit substrate to form a test structure having an electrically isolated semiconductor layer at a substrate surface, receiving the substrate at a measurement station, successively excluding a plurality of semiconductor sublayers from the surface of the semiconductor layer, making a respective sheet resistance measurement of the semiconductor layer after the exclusion of each of the plurality of sublayers to provide a plurality of resistance measurements, calculating a resistivity profile for the semiconductor layer from the plurality of resistance measurements, and after making the plurality of resistance measurements, performing at least one additional processing step on the substrate in the fabrication of integrated circuits on the substrate.

In another aspect, the invention is directed to a method of characterizing a semiconductor layer. The method includes receiving at a measurement station a substrate that includes a structure having an electrically isolated semiconductor layer at a substrate surface, successively excluding a plurality of semiconductor sublayers from the surface of the semiconductor layer while the substrate is at the measurement station, making a respective sheet resistance measurement at the measurement station of the semiconductor layer after the exclusion of each of the plurality of sublayers to provide a plurality of resistance measurements, and calculating a resistivity profile for the semiconductor layer from the plurality of resistance measurements.

In still another aspect, the invention is directed to a method of characterizing a semiconductor layer. The method includes receiving at a measurement station a substrate that includes a structure having an electrically isolated semiconductor layer at a substrate surface, successively oxidizing a plurality of semiconductor sublayers from the surface of the semiconductor layer to provide an oxidized portion on the surface of the substrate, making a respective sheet resistance measurement of the semiconductor layer after the exclusion of each of the plurality of sublayers and while the oxidized portion is on the surface of the substrate to provide a plurality of resistance measurements, and calculating a resistivity profile for the semiconductor layer from the plurality of resistance measurements.

In yet another aspect, the invention is directed to a method of characterizing a semiconductor layer, including receiving at a measurement station a substrate that includes a structure having an electrically isolated semiconductor layer that provides a van der Pauw resistor having a central portion and four arms extending from the central portion at a substrate surface, successively excluding a plurality of semiconductor sublayers in the central portion of the van der Pauw resistor, making a respective sheet resistance measurement of the semiconductor layer after the exclusion of each of the plurality of sublayers by making electrical contact to arms of the van der Pauw resistor to provide a plurality of resistance measurements, and calculating a resistivity profile for the semiconductor layer from the plurality of resistance measurements.

In still another aspect, the invention is directed to a method for characterizing layers in semiconductor substrates that includes using anodic oxidation to convert a layer of a semiconductor substrate into an anodic oxide layer in a test region defined on the surface of the substrate, and measuring a sheet resistance in the test region including the anodic oxide layer.

Implementations of any of the above inventions may include one or more of the following features in any combination. An initial sheet resistance of the conduction circuit may be measured prior to removal of any surface layers. Removal of the layers from the conductive circuit may be accomplished by repeated or continued anodic oxidation of the surface. Anodic direct current may be applied between a cathode and the test structure with a constant current source, and an incremental forming voltage maybe measured and used to determine a thickness of a removed surface layer. Anodic oxidation may be carried out on a small area where the test structure is located. The resistor test structure may be a cross van der Pauw resistor. The anodic oxidation may be is confined to the intersection of the arms of the cross van der Pauw resistor. Measuring the sheet resistance measurement may be performed without removing a surface oxide or an overlying electrolyte. A dopant concentration distribution of the pn structure or silicon surface layer may be calculated from the resistivity profile. The dopant concentration distribution may be calculated on the basis of specific mobility data, or on the basis of algorithms, such as A.S.T.M.

Standard F723. Sheet resistance may be measured by applying an alternating current through two arms of the van der Pauw resistor and measuring the voltage drop across the contacts on the opposite two arms. Removing surface layers from the conduction circuit may be carried out non-destructively on a production wafer such that the production wafer can be returned to the production process. A magnetic field may be applied to the resistor test structure and Hall sheet coefficients may be measured. A mobility profile may be calculated from from the Hall sheet coefficients. The semiconductor substrate may include a silicon substrate. A receptacle may be positioned over the test region to define an opening to the test region within a limited area, an electrolyte may be added into the receptacle positioned over the test region, the electrolyte may contact the test region in the limited area, and an electric current may be applied through the electrolyte and the substrate. A seal may be formed between the substrate and the opening of the receptacle. The electrolyte may includes an aqueous solution or a non-aqueous solution. Measuring the sheet resistance may include measuring a sequence of values for the sheet resistance, each value measured for the sheet resistance at a different depth of the anodic oxide layer. A respective depth of the anodic oxide layer may be determined for each value measured for the sheet resistance. A predetermined electric current may be applied between a cathode and the substrate to convert the layer of the substrate into the anodic oxide layer. The depth of the anodic oxide layer may be determined based on a voltage drop between the cathode and the substrate. One or more values of a differential resistivity may be determined based on two or more of the values measured for the sheet resistance, each value of the differential resistivity being determined for a respective depth in the substrate. A dopant distribution in the substrate may be estimated based on the determined values of the differential resistivity. The sheet resistance may be measured while the layer of the substrate is converted into the oxide layer. The conversion of the layer of the substrate into the oxide layer may be suspended while the sheet resistance is measured. The test structure may include a van der Pauw resistor. The test structure includes a central portion and four elongated arms attached to the central portion. A test current may be passed through two adjacent arms of the test structure and a voltage across two of the remaining arms of the test structure may be measured to determine the sheet resistance. The test current may be alternating current. A magnetic field may be applied to the test region, and a Hall sheet coefficient may be measured. A positive magnetic field may be applied to the test region and a first Hall sheet coefficient may be measured, and a negative magnetic field may be applied to the test region and a second Hall sheet coefficient may be measured. A sequence of values for the Hall sheet coefficient may be measured, each value measured for the Hall sheet coefficient at a different depth of the anodic oxide layer.

The invention also includes systems and computer-readable media to perform these methods.

It is understood that it is possible to carry out other electrical measurements such as capacitance/voltage or current/voltage sequentially after each increment of anodic oxide growth. These could be used to determine the dopant concentration, although such techniques appears more complex and difficult than the embodiment described herein.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

As a brief overview of one implementation, to determine the resistivity profile and the dopant concentration distribution of a silicon layer, e.g., an ultra-shallow junction, an outer surface semiconductor layer of a test structure is gradually converted to oxide, e.g., by anodic oxidation. As the oxidation progresses, a series of measurements made of the sheet resistance of the semiconductor layer (the series of measurements can be made at ever increasing thickness of the oxide portion, and thus at ever decreasing thickness of the silicon layer). These resistance measurements can be used to calculate the resistivity of the silicon layer as a function of depth (i.e., prior to oxidation). The resistivity profile of the silicon layer in the test structure thus provides useful information on the resistivity profile of other doped regions in the wafer (assuming that the dopant concentration is uniform across the wafer).

Figure 1A:
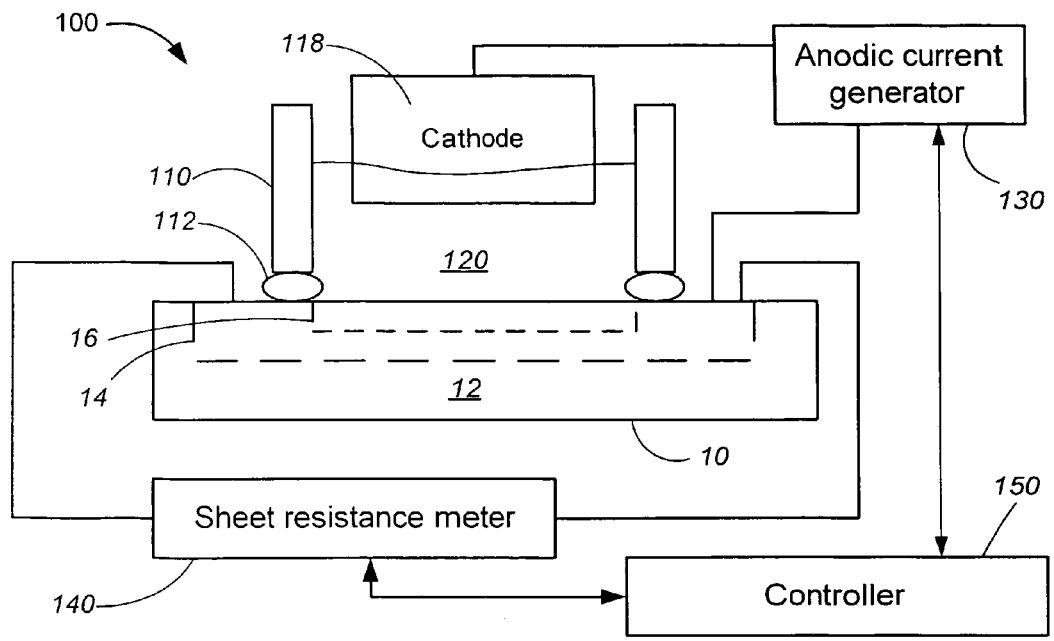
FIG. 1A is a schematic diagram illustrating a system that uses anodic oxidation and measures sheet resistance to characterize layers in a semiconductor substrate.

FIG. 1A illustrates a system 100 that uses anodic oxidation to characterize a substrate 10 that includes an underlying layer 12 and, at a surface of the substrate 10, a semiconductor layer 14 that is electrically isolated from the underlying layer 12. In one implementation, the substrate 10 is a silicon substrate and the semiconductor layer 14 is isolated from the underlying layer 12 by an interface between p-doped and n-doped layers. For example, the underlaying layer 12 can be a p-doped layer and the isolated layer 14 can be an n-doped layer, or vice versa. Alternatively, the substrate 10 can be a silicon-on-insulator ("SOI") substrate, and the semiconductor layer 14 can be isolated by the insulating layer of the SOI substrate.

To perform the anodic oxidation, the system 100 includes a receptacle 110 that contains an electrolyte 120 that is in contact with the substrate 10 over a test area. The electrolyte is confined to the test area using a seal, such as an o-ring 112. The electrolyte 120 is in contact with a cathode 118 that is used to drive an anodic current through the electrolyte 120 and the semiconductor layer 14 by an anodic current generator 130. The current generator 130 can be configured to maintain a predetermined constant anodic current by adjusting the voltage applied between the cathode 118 and the semiconductor layer 14. Optionally, the system 100 can include a light source to direct light to a portion of the test area to affect, e.g., increase, the rate of oxidation of the substrate.

The anodic current converts a portion of the semiconductor layer 14, e.g., a sublayer of generally uniform thickness at the top surface of the semiconductor layer 14, into an oxide layer 16 that is formed between the electrolyte 120 and the remaining portion of the semiconductor layer 14. As the oxidation progresses, the thickness of the oxide layer 16 grows and the converted portion extends deeper into the semiconductor layer 14. In alternative implementations, the sublayer is removed from the semiconductor layer 14. For example, the electrolyte 120 can include components that dissolve, e.g., etch, the oxide layer 16. In another alternative implementation, the sublayer can be removed, e.g., by chemical etching, without conversion to an oxide. Either by removing or converting into oxide, the sublayer is excluded from the semiconductor layer 14.

The system 100 includes a sheet resistance meter 140 that measures sheet resistance of the isolated semiconductor layer 14 in the test area, where the oxide layer 16 is formed. The oxide layer 16 is an insulator that has a substantially larger resistance than the semiconductor layer 14, for example, a doped silicon layer. In addition, the oxide layer 16 can insulate the semiconductor layer from the electrolyte. Thus the measured sheet resistance will depend substantially only on the semiconductor layer 14, whose thickness in the test area depends on the thickness of the oxide layer 16. In alternative implementations, where the semiconductor layer 14 is thinned by removing a sublayer and the electrolyte or etchant is in contact with the semiconductor layer, the sheet resistance calculation can be configured to take into account contributions of parallel conducting paths through the electrolyte or etchant. However, such conducting paths can decrease the precision of the sheet resistance measurements.

To measure sheet resistance, the sheet resistance meter 140 can pass a resistor current through the isolated semiconductor layer 14, and can measure a voltage that is generated by the current between two separate locations in the semiconductor layer 14. For example, the voltage can be measured between the two points where the resistor current enters and leaves the semiconductor layer 14, and the sheet resistance meter 140 can calculate the sheet resistance based on a geometrical shape of the semiconductor layer 14 in the test area. Alternatively, the voltage can be measured at locations that are different from those at which the resistor current enters and leaves the semiconductor layer 14. For example, the sheet resistance can be measured with a four-point probe or the test area can include a van der Pauw resistor structure, as discussed below with reference to FIG. 2.

The system 100 also includes a controller 150 that can control the system, collect the anodic oxidation and sheet resistance data, and determine the resistivity as a function of depth to provide the resistivity profile measurements. Based on the resistivity profile, if the semiconductor layer 14 is doped with dopants whose mobility is known, the controller can also calculate dopant concentration distributions as a function of depth (without using the data obtained with the magnetic fields as discussed below with reference to FIGS. 1A and 3A). The controller 150 can be implemented using a computer executing instructions of one or more computer program products, or the controller 150 can be implemented by hardware such as a programmable control array.

The controller 150 can instruct the anodic current generator 130 to set a particular anodic current and monitor the voltage that is applied to maintain the set anodic current or time period during which the anodic current is applied. Based on the applied voltage or time period, the controller 150 can determine a thickness of the oxide layer 16 or the thickness removed from the semiconductor layer 14, as further discussed with reference to FIGS. 4 and 5.

The controller 150 can also instruct the sheet resistance meter 140 to perform a sequence of measurements that correspond to a sequence of different thicknesses of the oxide layer 16. If the voltage applied by the anodic current generator 130 is controlled, the controller 150 can instruct the sheet resistance meter 140 to perform the measurements at predetermined values or predetermined steps of the applied voltage. Alternatively, the sheet resistance can be measured at predetermined time intervals. The sheet resistance measurements can be performed while the anodic current is flowing, or the controller 150 can instruct the anodic current generator 130 to pause the anodic current during the sheet resistance measurements. The controller 150 receives the sheet resistance measurements from which the controller 150 can calculate a resistivity profile based on the depth of the sublayer that is excluded from the semiconductor layer 14.

Figure 2:
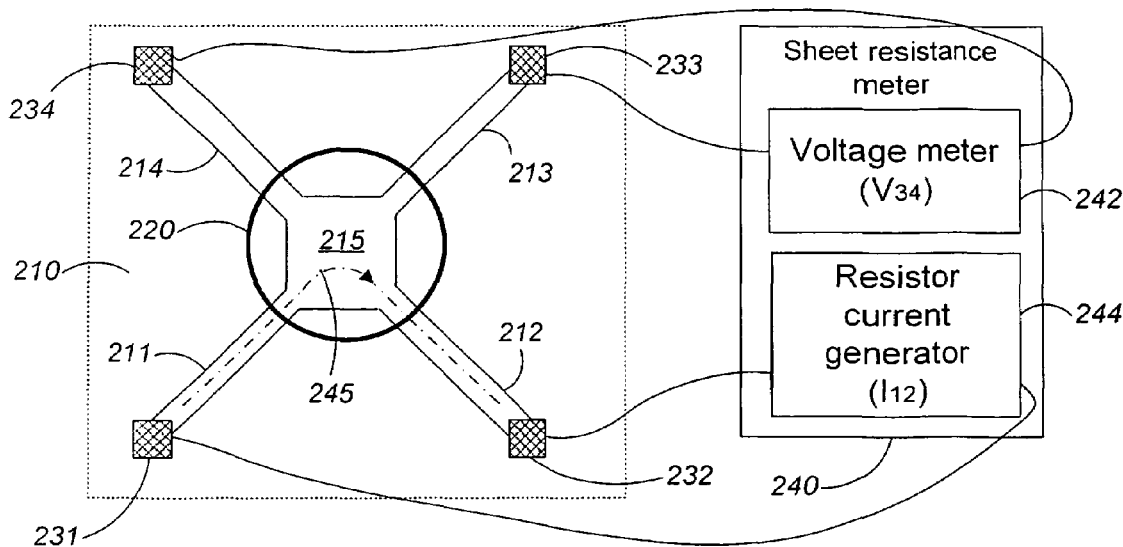
FIG. 2 is a schematic diagram illustrating an example test structure for measuring the structure's sheet resistance, with or without an applied magnetic field.

FIG. 2 illustrates an example test structure 210 that is formed on a surface of a semiconductor substrate and a sheet resistance meter 240 to measure resistivity profile in the test structure 210 using anodic oxidation. In the system 100 (FIG. 1A or 11B), the test structure 210 can be formed on the substrate 10 and the sheet resistance meter 240 can be used as the sheet resistance meter 140.

The test structure 210 can be formed by any one of several techniques that are used in device manufacture. These techniques include implantation and diffusion through oxide masks, implantation through photoresist masks and silicon etching around a test structure protected by oxide or photoresist. Examples for different test structures are further discussed with reference to FIGS. 6A–6D.

The test structure 210 implements a van der Pauw resistor, and includes a central portion 215 and four arms 211, 212, 213 and 214 extending from the central portion 215. A test area 220 is defined by a receptacle that contains an electrolyte that is in contact with the substrate within the test area 220. The test area 220 includes the entire central portion 215 whose sheet resistance will be measured after being oxidized by an anodic current flowing through the electrolyte.

The sheet resistance meter 240 includes a voltage meter 242 and a resistor current generator 244. The sheet resistance meter 240 is electrically connected to the test structure 210 by electric contacts 231–234 that are formed on the four arms 211–214 of the test structure 210. The resistor current generator 244 passes a resistor current 245 through any two adjacent arms, e.g. the first and second arms 211 and 212 of the structure 210, and the voltage meter 242 measures a corresponding voltage at two different locations, at the third and fourth arms 213 and 214. Based on the value $I_{12}$ of the resistor current 245 and the value $V_{34}$ measured by the voltage meter 242, the sheet resistance can be calculated using standard formulas, as discussed below with reference to an experimental implementation. By using the van der Pauw resistor, the measured sheet resistance is independent of the shape of the measured region. Thus the test structure 210 can provide high precision results without using high precision techniques or equipment to form the test structure 210.

Figure 3A:
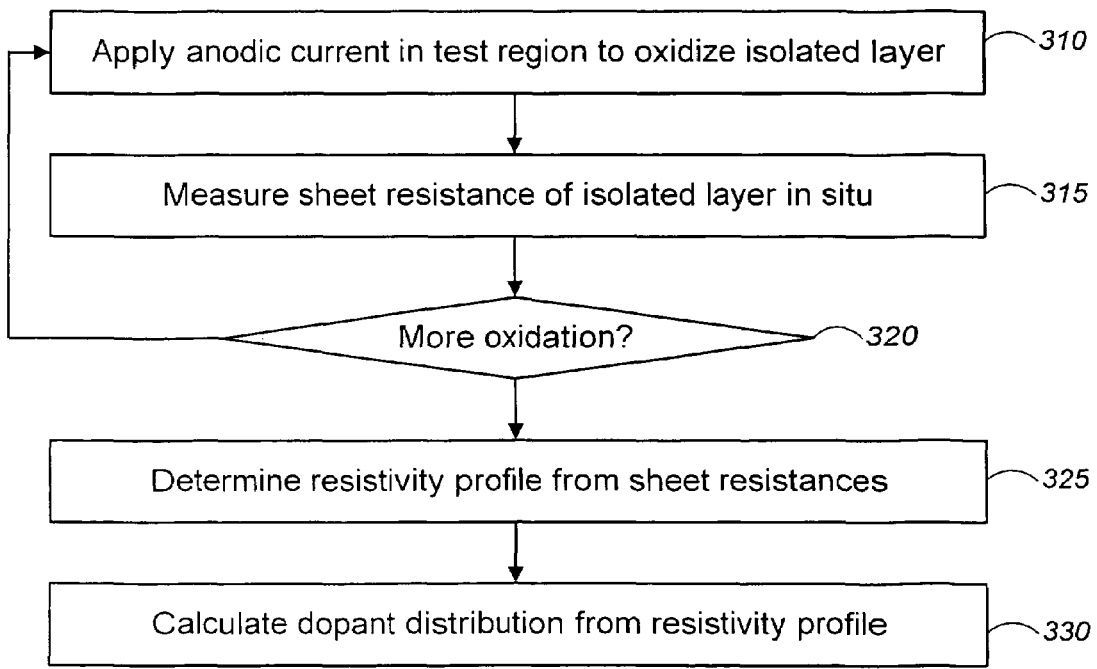
FIGS. 3A and 4 are schematic flow diagrams illustrating methods for using anodic oxidation to characterize layers in a semiconductor substrate.

FIG. 3A illustrates a method 300 for using anodic oxidation to characterize layers, such as pn-junctions in a semiconductor substrate. The substrate includes a test structure defining an isolated semiconductor layer in a test area where the anodic oxidation will be applied. The method 300 can be performed by the system 100.

The system applies an anodic current in the test area to oxidize a sublayer of the semiconductor layer using anodic oxidation (step 310). The anodic current is applied by a cathode through an electrolyte that is in contact with the test area. The electrolyte is contained in a receptacle that confines the oxidation to the test area. Alternatively, the electrolyte can contact a substrate region that is larger than the test area.

The applied anodic current can be a predetermined DC current that is maintained by a current generator. If the generated oxide remains on the test structure, the predetermined current is maintained by a voltage that increases with an increasing thickness of the oxide layer, as further discussed with reference to FIGS. 4 and 5. Alternatively, the applied anodic current can be generated by a predetermined voltage between the cathode and the substrate. If the generated oxide is dissolved from the test structure, the anodic current can be applied for a predetermined time period.

The system measures sheet resistance in the test area in situ, that is, without removing the substrate from the measurement station where the anodic current is applied to the test area (step 315). The sheet resistance can be measured while the oxidation current is applied, or the oxidation current can be turned off during the measurement. In one implementation, the test structure includes a van der Pauw resistor having four or more arms. Alternatively, the sheet resistance can be measured by other resistor designs, such as designs that require the entire resistor area to be oxidized.

The system determines whether more oxidation is required (decision 320). For example, for a constant anodic current, the system can verify whether the voltage applied to maintain the constant current has reached a predetermined value, and continue to apply the anodic current until the voltage reaches the predetermined value. Alternatively, the system can apply the oxidation current for a predetermined time period. If further oxidation is required ("Yes" branch of decision 320), the system further applies the anodic current (returns to step 310).

Figure 9A:
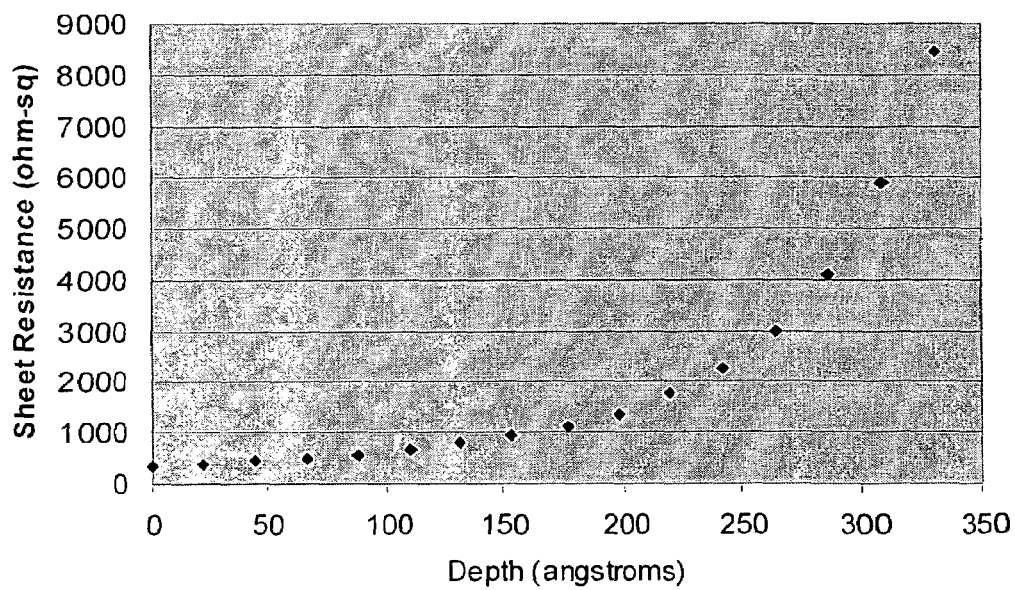
FIGS. 9A–9C are diagrams illustrating results of example measurements of sheet resistance, resistivity profile, and distribution of dopant concentration.

If no more oxidation is required ("No" branch of decision 320), the system determines a resistivity profile from the measured sheet resistances (step 325). First, a sheet resistance profile is determined. The sheet resistance profile associates the measured sheet resistances with a corresponding depth of all the sublayers excluded by the oxidation. If the oxide layer remains on the test structure, the depth values can be determined from the voltage applied to maintain the predetermined anodic current. Alternatively, the depth values can be determined by other in-situ measurements, such as an optical measurement of the oxide thickness. Alternatively, the depth can be determined as a function of time based on prior experimental measurements. The controller can store a function such as a look-up table or an equation that converts the parameter, e.g., anodic voltage or time, to depth. Optionally, the sheet resistance profile can be noise filtered, smoothed or otherwise processed. An example experimental sheet resistance profile is illustrated in FIG. 9A.

Figure 9B:
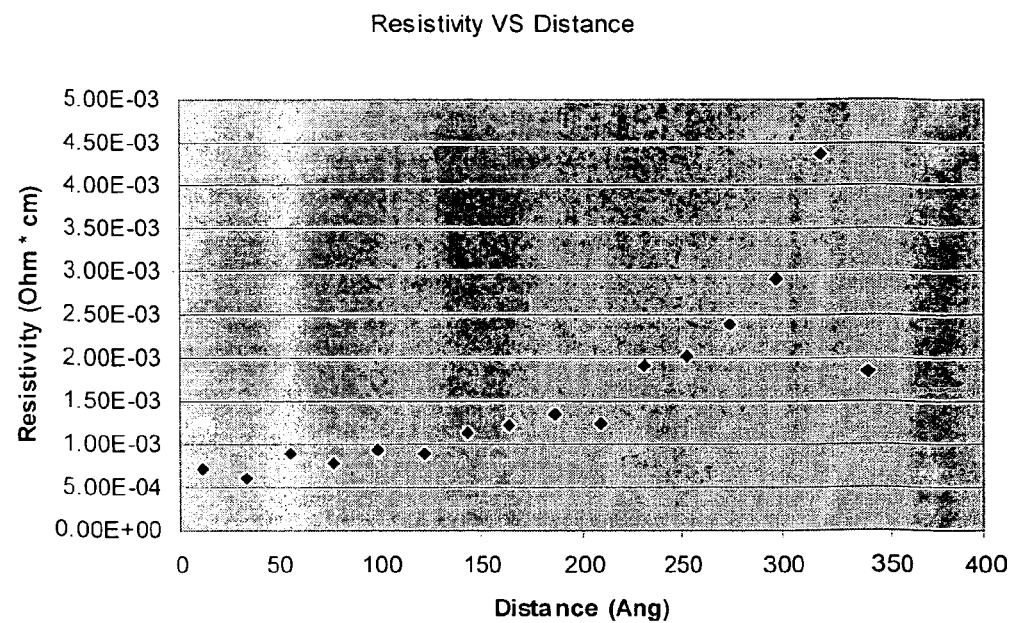

From the sheet resistance profile, the system determines the resistivity profile. The resistivity profile defines a respective resistivity (that is, resistance for a unit length and unit cross section) at different depth values of the sublayer that is converted into an anodic oxide layer (or otherwise excluded, for example, removed, from the conductive paths in the test structure). Alternatively, if the thickness of the insulated semiconductor layer is known before the oxidation, the resistivity profile can also specify resistivities as a function of the remaining thickness of the semiconductor layer in the test structure. An example experimental resistivity profile is illustrated in FIG. 9B.

Figure 9C:
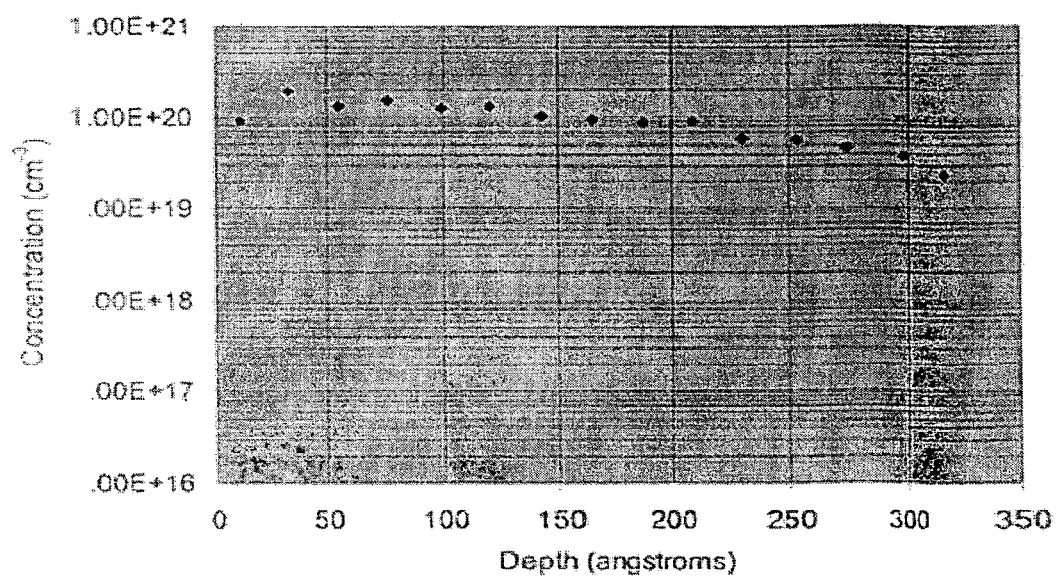

The system can also calculate a dopant distribution from the resistivity profile (step 330). The dopant distribution can be calculated based on the dopant's assumed mobility or other parameters of the test structure. For example, the system can take into account space charge effects at interfaces between different layers. An example experimental concentration is illustrated in FIG. 9C.

Referring to FIG. 1A, in another implementation, the system 100' includes a permanent magnet 124, which can be placed in or removed from a position under the test area on the semiconductor layer 14. In the system 100', the meter 140 can measure both sheet resistance and Hall sheet coefficients of the isolated semiconductor layer 14 in the test area.

When in place, the magnet generates a substantially uniform magnetic field that extends through the test area on the semiconductor layer 14. The magnet can be rotated by 180 degrees to reverse the magnetic field from positive to negative (or vice versa). Thus, by including one or more magnets in the system, it is possible to carry out sheet Hall coefficient measurements under conditions of a positive or negative magnetic field. For example, a small robotic actuator could move the magnet into place for the first Hall coefficient measurement, rotate the magnet by 180 degrees for the second Hall coefficient measurement, and then move away from the test area for the conventional sheet resistance measurement. Alternatively, the system could include two magnets with opposing magnetic fields that would be swapped. As yet another alternative, the system could include an electromagnet that can be switched on and off, or reversed in polarity.

Figure 3B:
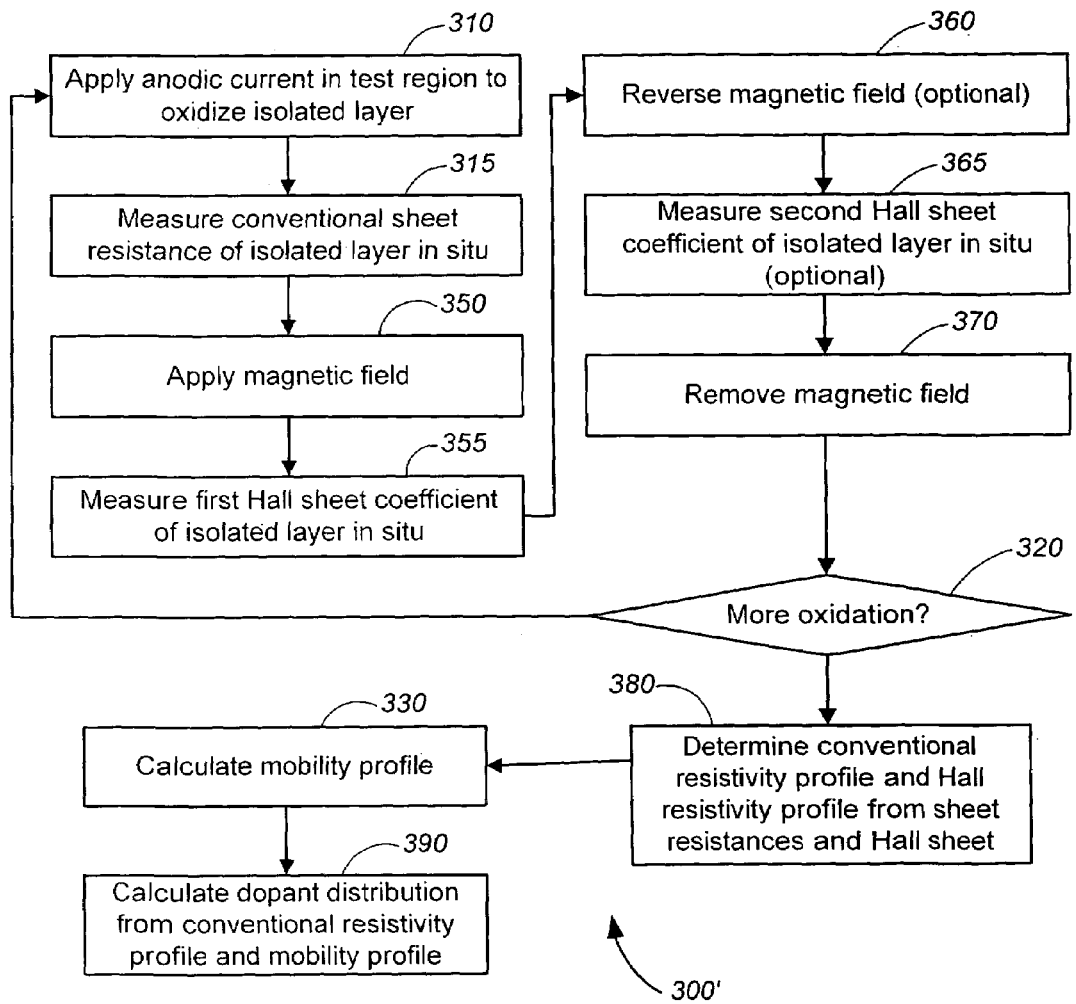
FIG. 3B is a schematic flow diagram illustrating a method for using anodic oxidation if Hall sheet coefficient measurements are available to characterize layers in a semiconductor substrate.

FIG. 3B illustrates a method 300' that is similar to the method 300 described above, but includes the measurement of Hall sheet coefficients. The system applies an anodic current in the test area to oxidize a sublayer of the semiconductor layer using anodic oxidation (step 310). The system can measure sheet resistance and the sheet Hall coefficient in the test area in situ, that is, without removing the substrate from the measurement station where the anodic current is applied to the test area. In particular, the conventional sheet resistance can be measured (step 315). A magnetic field is applied (step 350), e.g., by moving the magnet into position adjacent the substrate with the actuator, and a first Hall sheet coefficient is measured (step 355) with a positive magnetic field. Then the magnetic field is reversed (step 360), e.g., by rotating the magnet by 180 degrees, and a second Hall sheet coefficient is measured (step 365) with a negative magnetic field. The magnetic field is removed (step 370) in preparation for the next conventional sheet resistance measurement. In one implementation, only one measurement is made with an applied magnetic field. It should be realized that the measurement steps need not be performed in the order shown, e.g., the measurement of the conventional sheet resistance could be before or after the measurement of the Hall sheet coefficients. As discussed above, the sheet resistance and the sheet Hall coefficient can be measured while the oxidation current is applied, or the oxidation current can be turned off during the measurement.

The system determines whether more oxidation is required (decision 320). If further oxidation is required ("Yes" branch of decision 320), the system further applies the anodic current (returns to step 310), and continues the series of measurements.

If no more oxidation is required ("No" branch of decision 320), the system determines a conventional resistivity profile and a Hall resistivity profile from the measured sheet resistances and the Hall sheet coefficients (step 380). First, the sheet resistance profiles are determined. The sheet resistance profiles associate the measured sheet resistances and Hall sheet coefficients with a corresponding depth of all the sublayers excluded by the oxidation. From the sheet resistance profiles, the system determines the resistivity profiles.

From the Hall resistivity profiles, the system can calculate a mobility profile (step 385). Finally, the system can calculate a dopant distribution from the conventional resistivity profile and the mobility profile (step 390). In contrast to steps 325 and 330, if both the conventional resistivity profile and Hall resistivity profiles have been calculated, it is possible to calculate the mobility directly.

Figure 1B:
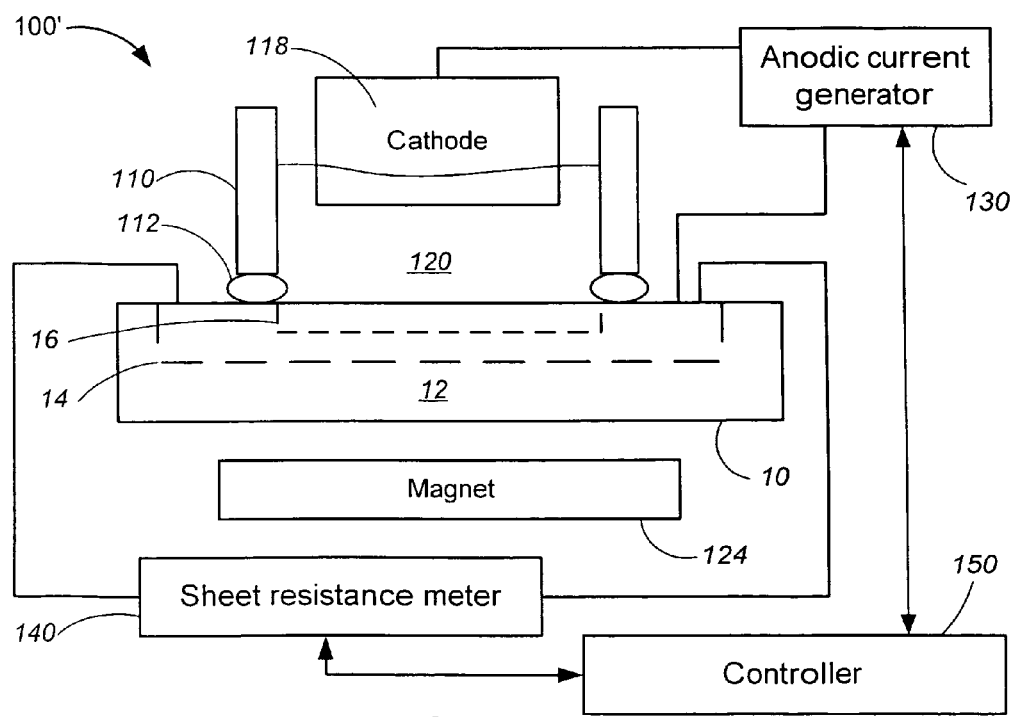
FIG. 1B is a schematic diagram illustrating a system that uses anodic oxidation and measures sheet resistance and Hall sheet coefficients to characterize layers in a semiconductor substrate.
Figure 4:
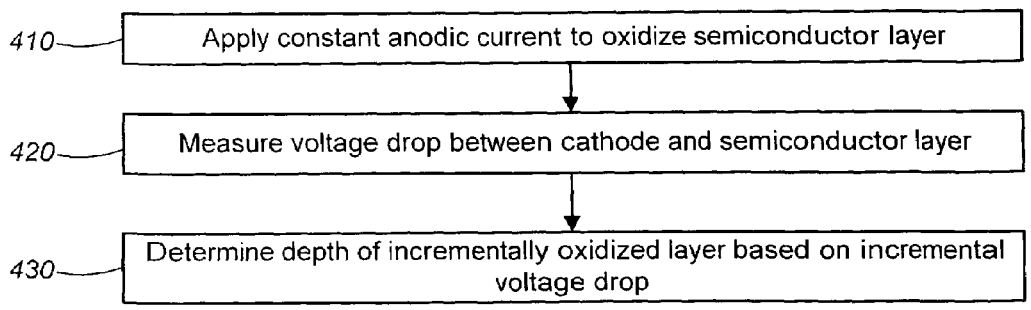

FIG. 4 illustrates a method 400 for determining the depth (thickness) of an oxidized sublayer that is in between an electrolyte and a semiconductor layer that is oxidized by an anodic current flowing through the electrolyte and the semiconductor layer. The anodic current enters the electrolyte through a cathode. The method 400 can be performed by the system 100 (FIG. 1A) or the system 100' (FIG. 1B.)

The system applies a constant anodic current to successively convert sublayers on the surface of the semiconductor layer into an oxide layer (step 410). The oxide layer remains on the semiconductor layer.

The system measures a voltage drop between the cathode and the semiconductor layer (step 420), and determines a depth of the oxidized layer based on the voltage drop (step 430).

Figure 5:
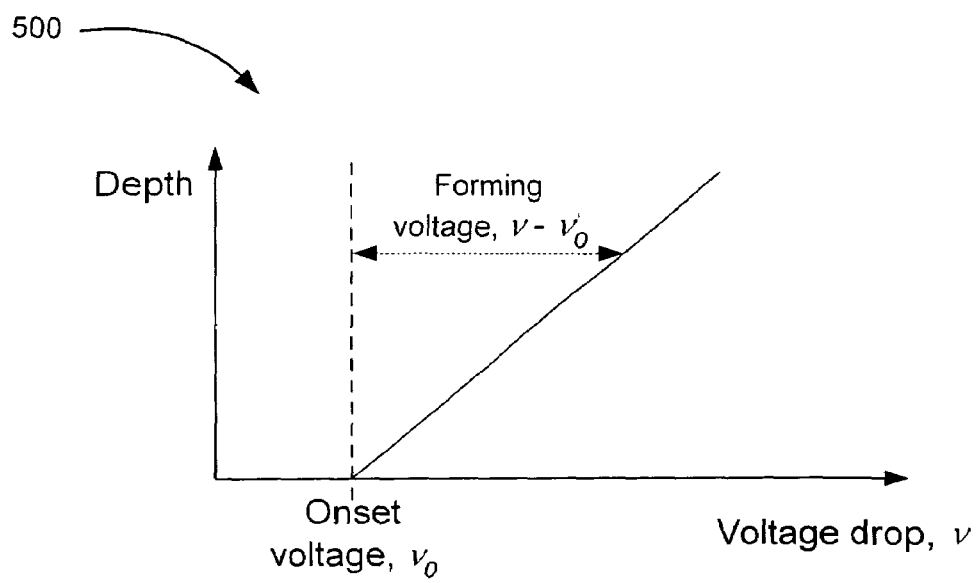
FIG. 5 is a schematic diagram illustrating a depth of an oxide layer as a function of voltage drop between the cathode and anode for a constant anodic oxidation current.

In FIG. 5, a diagram 500 illustrates a schematic dependence of the depth of the oxidized layer as a function of the voltage drop between the cathode and the substrate for a constant anodic current. The anodic oxidation starts at an onset voltage $V_0$, and the depth of the oxide layer is substantially proportional to a forming voltage $V-V_0$ that is measured from the onset voltage $V_0$. The depth (thickness) of the oxide layer is proportional to the thickness of the semiconductor sublayer from which the oxide layer is formed. The exact relation is defined by structural properties of the semiconductor and oxide materials.

FIGS. 6A–6D illustrate cross sections of example test structures formed on a substrate to characterize resistivity profiles in semiconductor layers, such as shallow and ultra shallow junctions or thin layers formed on SOI substrates.

Figure 6A:
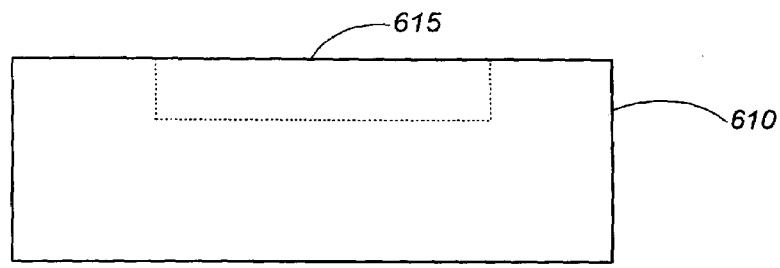
FIGS. 6A–6D are schematic diagrams illustrating cross sections of exemplary test structures on a semiconductor substrate.
Figure 6B:
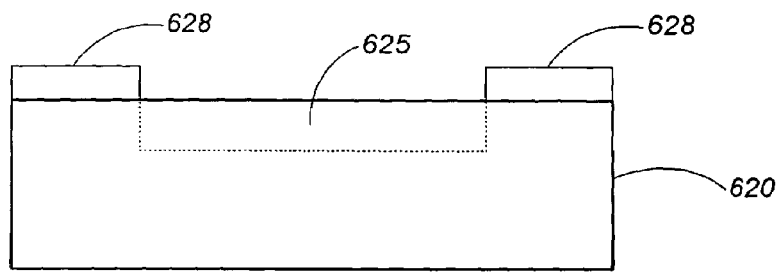
Figure 6C:
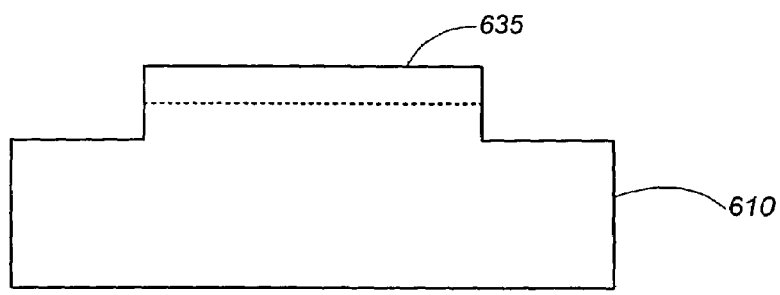

FIGS. 6A–6C illustrate pn junctions that are created by introducing dopants into localized areas 615, 625 and 635 of respective semiconductor substrates 610, 620 and 630. For example, the semiconductor substrate 610, 620 or 630 can be a lightly n-doped substrate and the corresponding localized area 615, 625 or 635 is p-doped, or vice versa (the semiconductor substrate 610, 620 or 630 is a lightly p-doped substrate and the corresponding localized area 615, 625 or 635 is n-doped). Such junctions can be formed using a mask, such as a photoresist mask or an oxide mask which acts to localize the dopants. As shown in FIG. 6B, a mask 628 can remain in the test structure. In one implementation a van der Pauw resistor is formed from a uniformly doped surface that is generated by a blanket diffusion or implantation. As shown in FIG. 6C, the resistor can be etched out using a pattern made of a surface protective covering such as photoresist or oxide.

Figure 6D:
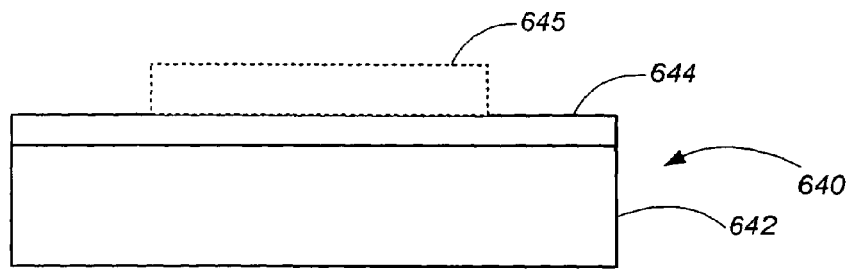

FIG. 6D illustrates an SOI substrate 640, where a thin layer 645 of semiconductor, such as an n or p doped silicon layer, is isolated from a substrate layer 642 by an insulating layer 644 of the SOI substrate 640. Because the thin semiconductor layer 645 is electrically isolated from the rest of the substrate, the resistivity profile can be evaluated in this test structure substantially the same way as for the shallow junctions discussed above.

Figure 7:
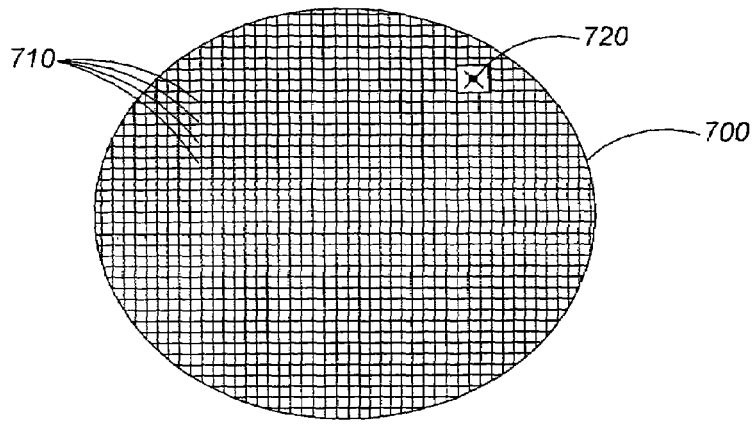
FIG. 7 is a schematic diagram illustrating an example wafer including a test structure for resistivity profiling.

FIG. 7 illustrates a wafer 700 that is an example of a production integrated circuit substrate. The wafer 700 includes a large number of integrated circuits 710 and a test structure 720. The test structure 720 can occupy a small fraction of the wafer 700, and can be used to characterize semiconductor structures, such as shallow junctions, on the wafer 700 during the fabrication of the integrated circuits 710. While the wafer 700 can have a diameter of several inches, the test structure 720 can have a characteristic size in the order millimeters or smaller. The test structure 720 can have shallow junctions that have the same layered structure, but occupy substantially larger surface area than the shallow junctions formed in the integrated circuits 710. Thus the test structure 720 can easily be accessed for measurements and can provide a convenient tool to characterize shallow junctions or other layered structures without destroying the entire wafer 700.

Figure 8:
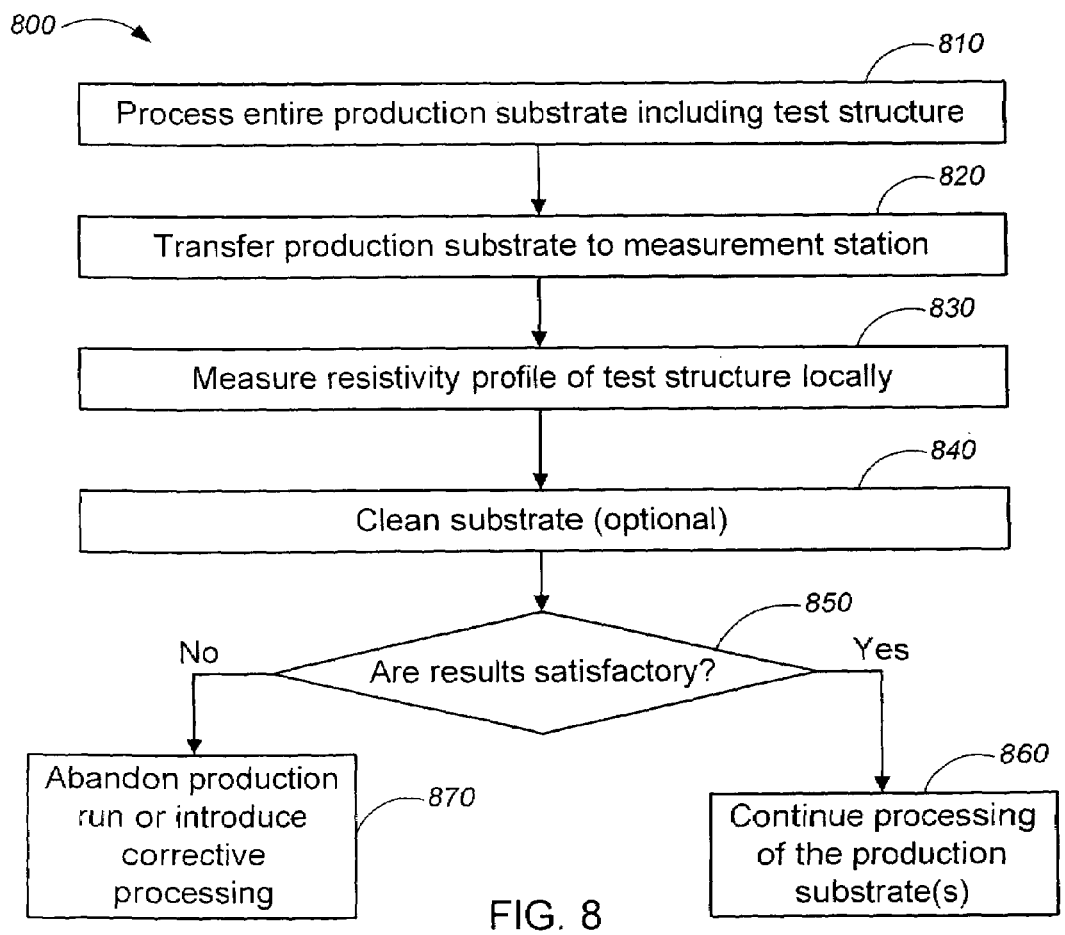
FIG. 8 is a schematic flow diagram illustrating a method for processing a production integrated circuit substrate including a test structure for resistivity profiling.

FIG. 8 illustrates a method 800 for characterizing a production integrated circuit substrate including a test structure, such as the test structure 210 for resistivity profiling (FIG. 2). The method 800 can be performed by a production system that includes a measurement station including the system 100 using anodic oxidation for resistivity profiling (FIG. 1).

The production system processes the entire production integrated circuit substrate that includes a test structure for resistivity profiling (step 810). The production substrate is transferred to the measurement station (step 820). For example, the production system can include a robotic arm to transport the wafer from a cassette or from another processing station in a processing tool to a wafer support in the measurement station. At the measurement station, the resistivity profile, mobility profile and/or dopant concentration can be determined locally for the test structure (step 830), as described above with reference to FIGS. 3A and 3B. The measurement is performed in situ, without removing the production substrate from the measurement station. At the measurement station, the test structure is identified on the production substrate and an electrolyte is applied locally, only to a portion of the test structure. Electrical contacts are made to the identified test structure, and the resistivity profile is measured. Optionally, the substrate can be cleaned after the measurement (step 840).

Once the resistivity profile, mobility profile and/or dopant have been determined, the system can determine whether the measurements are satisfactory (step 850), e.g., by comparing the profiles to target profiles.

Although the test structure is oxidized during the measurement, the rest of the production substrate is not destroyed by the measurement. Thus if the measurement provides satisfactory results ("Yes" branch of decision 850), the production substrate can be returned from the measurement station back to the fabrication process, where one or more additional processing steps are performed to fabricate integrated circuits on the production substrate (step 860). Assuming that other substrates in the production lot have undergone identical processing and have dopant concentrations that are substantially uniform wafer-to-wafer, the test can characterize not just the single test structure or single substrate, but all the substrates in the production lot. Thus, other substrates from the production lot can be passed to the next processing step without undergoing the measurement procedure.

If the measurement results are not satisfactory ("No" branch of decision 850), it may be necessary to adjust downstream processing steps or to abort the run (step 870). In addition, it may be possible to adjust the doping process for other substrates in the production lot that have yet to undergo the doping process (this can be combined with discarding substrates or adjusting downstream processing steps for substrates in the production lot that have already undergone the doping process).

Thus the resistivity profile or dopant concentration distribution regarding the wafer can be fed forward to a control algorithm in a later tool in the process to provide data to control the processing parameters for that wafer, or fed back to a control algorithm in an earlier tool in the process to provide data to control processing of subsequent wafers. Thus based on the measurement results, the production system can be corrected without long delays, or without producing a large number of unsatisfactory integrated circuits.

EXPERIMENTAL IMPLEMENTATION

Sample Preparation

The test structures used to evaluate this technique were prepared on the surfaces of wafers which had been subjected to blanket implantations. N-type wafers with a donor concentration of $2\times10^{14}$ cm$^{-3}$ were implanted with a dose of $1\times10^{15}$ BF$_2$ cm$^{-2}$ at an energy of 5 keV. P-type wafers with an acceptor concentration of $1\times10^{15}$ cm$^{-3}$ were implanted with a dose of $1\times10^{15}$ As cm$^{-2}$ at an energy of 2 keV. These wafers were subjected to a rapid thermal anneal of 10 seconds at 1000 degrees Celsius.

The test structures were prepared by applying photoresist to the surfaces, and applying UV light through a mask, which delineated the test pattern. After the development of this pattern, the use of XeF$_2$ gas etching, a standard production technique, produced test structures similar to that as shown in FIG. 2 with a cross-section as shown in FIG. 6C.

Apparatus

Four items of equipment were used. The first was a mount for the specimen. The van der Pauw resistor was prepared on a silicon square 2 cm×2 cm. This square was attached to a larger sheet of circuit board which was prepared to conduct current to the four van der Pauw contacts. For a production model a micromanipulator probe station with tungsten wire probes was used to provide contact for both anodization and sheet resistance measurements.

An Hp 6186B DC current source capable of delivering up to 100 ma at voltages up to 300V was used to power the anodization and a digital multimeter was used to monitor the voltage. Our current source was nominally limited to 300V. A current source with a 500V limit can be used to measure deeper junctions. The sheet resistance measurements were carried out with a Princeton Applied Research 124A lock-in amplifier.

Anodization Setup

The receptacle for the electrolyte was placed on the silicon surface so that the O-ring surrounds the test structure. The O-ring used in this embodiment had an 0.5 mm diameter. The electrolyte was introduced into the receptacle to a level that is in contact with the metallic cathode rod after vertical pressure is first applied to the O-ring to insure that the electrolyte will be confined to its receptacle. The metallic cathode rod was selected to avoid chemical reactions with electrolyte. The cathode can be plated with gold or platinum. We used a stainless steel rod for our cathode. For production use it may be desirable to avoid the introduction of iron. Another metal such as titanium can also be used. Both aqueous and non-aqueous solutions have been satisfactorily used to grow anodic oxide. For the non-aqueous solutions, the use of polar liquids such as ethylene glycol, N-methylacetamide, and tetrahydrofurfuryl alcohol were previously evaluated. We used ethylene glycol, prepared according to the following proportions:

| | |
|---|---|
| Ethylene glycol | 58 ml |
| KNO$_3$ | 230 mg |
| Al(NO$_3$)$_3$·9H$_2$O | 87 mg |
| H$_2$O | 0.29 ml |

For production use, it may be desirable to avoid the introduction of potassium. Another nitrate such as C$_s$NO$_3$ or NH$_4$NO$_3$ can also be used instead of or in addition to KNO$_3$.

Electrical Contacts

Electrical contacts to the test structure serve two purposes, to evaluate the sheet resistance of the doped layer and to conduct the current that causes the growth of the anodic oxide. Electrical contacts were made either with Ag-filled epoxy, which assured good ohmic contact, or with tungsten wire probes that can also be used for non-destructive testing of a silicon wafer during processing. Our technique can be used to evaluate ultra-shallow junctions, which requires special attention to the use of low-pressure wire probes to avoid shorting through the junction lying just beneath the surface. We used the 7F-C310-Pt and 7F-C310-Au probes supplied by the Micromanipulator Company for measuring the sheet resistance of the test structures. For the contact which carried the much heavier anodic current to the silicon substrate, we used the 00–1800-R-XX Micromanipulator probe. The electrical contacts made with Ag-filled epoxy could be used for both the anodic current and the sheet resistance measurements.

Testing Procedure

The current density used in growing the anodic oxide determines the rate of oxide growth. We chose a current density of 10 ma/cm$^2$, which resulted in a rate of anodic oxide growth of approximately 50–100 angstroms per minute.

The voltage drop between the metal cathode and the silicon surface was monitored during the anodic oxidation. This voltage drop is the sum of the voltage drop across the electrolyte and the test specimen and the forming voltage developed across the silicon dioxide, which forms over the silicon surface. The voltage drop at the onset of the anodic oxidation is noted as $V_o$. The incremental increase of the voltage, $V-V_o$, is referred to as the forming voltage and is a linear function of the thickness of the anodic oxide. We found an initial voltage drop of 30–50V and a rate of anodic oxide growth of 5 angstroms of oxide for each 1 volt of forming voltage. This relationship may be refined with continued measurements.

To convert the oxide thickness to the equivalent silicon layer consumption we use the value of 44% established for thermal oxidation. This corresponds to a ratio of 2.2 angstroms per volt of forming voltage. For anodic oxide formation, this value may be slightly lower.

Electrical contacts for the sheet resistance measurements were made at points 1, 2, 3 and 4 corresponding to contacts 231–234 shown in FIG. 2. For the van der Pauw measurement, current is passed through two adjacent contacts such as 1 and 2, 2 and 3, 3 and 4, or 4 and 1. The voltage is measured across the opposite two contacts. Thus for $I_{12}$ the current is passed between contacts 1 and 2, and the voltage, $V_{34}$ is measured across contacts 3 and 4. For both the Ag epoxy and tungsten wire contacts we used a resistor current of 14.1 na. With this current across contacts 2 and 3, we measured the voltage drop, $V_{14}$, across contacts 1 and 4. With the current across contacts 1 and 4 we measured $V_{23}$, the voltage across contacts 2 and 3.

A.S.T.M. standard F76 recommends that all eight possible measurements be carried out on the van der Pauw resistor and that an average value be used. For a symmetrical van der Pauw design as shown in FIG. 2, and using AC rather than DC, we formed that measure values tracked one another closely and that it was possible to carry out accurate calculations using four, two, or even just one measurement.

We define our resistor voltages as follows:

$V_{12}$ with $I=I_{34}$, the AC current across contacts 3 and 4
$V_{23}$ with $I=I_{41}$, the AC current across contacts 4 and 1
$V_{34}$ with $I=I_{12}$, the AC current across contacts 1 and 2
$V_{41}$ with $I=I_{23}$, the AC current across contacts 2 and 3

Assuming that $I_{12}=I_{23}=I_{34}=I_{41}$, the sheet resistance R is defined as follows $$R = f \bullet (V_{12} + V_{23} + V_{34} + V_{41}) \frac{4.53}{4I}$$

where I is the AC current across the contacts.

If $V_{12} \cong V_{23}$ and $V_{34} \cong V_{41}$, then $f=1$.

We measure the Hall sheet coefficient identically to the way we measured the sheet resistance but under the different external condition, i.e., with a positive magnetic field (B) and a negative magnetic field (–B) of equal intensity.

The definition of Hall sheet coefficient is as follows:

$$RH = \frac{2.50 x 10^7}{2B \cdot I}$$
$$[V_{12}(+B) + V_{12}(-B) + V_{23}(+B) + V_{33}(-B) + V_{34}(+B) + V_{34}(-B) + V_{41}(-B)]$$

where B is the magnetic field intensity in gauss, I is the AC current in amperes, $V_{12}$, $V_{23}$, $V_{34}$, and $V_{41}$ are voltages defined above in volts, and RH is the resulting Hall sheet coefficient in $cm^2$/coulomb.

When voltages track each other and we reduce the voltage measurements from eight to four or less, it is possible to use a positive magnetic field only.

We began by measuring the sheet resistance of the test structure in air. Once the anodic oxidation began, we measured the sheet resistance at 10 volt increments of forming voltage corresponding to 22 angstrom silicon layer depths. To avoid photoelectric effects, the electrical measurements were carried out in the dark.

As the overlying anodic oxide grew in thickness, we noted that our voltage measurements became unstable, changing slowly with time. We attributed this to the drift of the anions in the anodic oxide layer and substituted an AC current for the DC current initially used. This permitted us to make precise measurements. Both 6 Hz and 100 Hz gave comparably satisfactory results.

Our objective was to establish a sheet resistance profile for the doped layer as shown in FIG. 9A. This consists of a series of sheet resistance evaluations at the original surface of the ultra-shallow junction and at successively deeper levels under the surface. Our first measurement of the test structure in air gives us a correct sheet resistance value as measured. Successive measurements can be effected by contact of the conductive doped layer with increasing thicknesses of anodic oxide and by contact with the electrolyte. Sheet resistance measurements of anodized test structures which were removed from the electrolyte were compared to measurements made in contact with the electrolyte. Sheet resistance measurements made with overlying anodic oxide were compared with measurements made from the same test structure from which the anodic oxide was stripped with dilute hydrofluoric acid.

We found that once anodic oxide had begun to grow on the surface, there was no effect due to contact with the electrolyte. Slight differences in the measured values with and without the oxide were within the experimental error.

By introducing resistance measurements under magnetic fields we can obtain a mobility profile in addition to the resistivity profile. This permits us to obtain a dopant concentration distribution directly without having to assume mobility values.

Calculations

Examining our experimental data, FIG. 9A. we note that the sheet resistance increases monotonically with the distances $X_1$, $X_2$ ... $X_{n-1}$, $X_n$ from the original surface until it reaches an unstable value which we interpret as signifying that an electrical junction no longer exists. The ratio of the first to the last value is 0.023, indicating that our readings describe 99.7% of the conductive cross-section. We can covert this data into a resistivity profile, using the following relationship:

$$\rho(n) = \frac{\Delta X}{[Rs(n-1)]^{-1} - [Rs(n)]^{-1}} \text{ ohm-cm}$$

where $\Delta X$ is the incremental thickness of layer n, and Rs(n) is the sheet resistivity measurement for layer n. This permits us to assign an average resistivity to each 22 Å thick silicon layer. The result is shown in FIG. 9B.

Such profiles provide information to characterize the ultra shallow junctions used in a CMOS transistor as they reflect the current carrying abilities of the source and drain structures.

If we also carry out similar measurements under conditions of an externally applied magnetic field, we can similarly obtain the Hall resistivity profile, $\rho H(n)$ using the following relationship:

$$\rho H(n) = \frac{\Delta X}{[RH(n-1)]^{-1} - [RH(n)]^{-1}} \text{ cm}^3/\text{coulomb}$$

where ΔX is the incremental thickness of layer n, and RH(n) is the Hall sheet coefficient measurement for layer n.

The Hall mobility, μH, is defined as follows:

$$\mu H = \frac{\rho H}{\rho} \frac{\text{cm}^3}{\upsilon - \text{sec}}$$

Thus, the mobility profile, μH(n) can be calculated as:

$$\mu H(n) = \frac{\rho H(n)}{\rho(n)} \frac{\text{cm}^3}{\upsilon - \text{sec}}$$

This is turn permits us to calculate directly the dopant concentration distribution, N(n), using the following relationship:

$$N(n) = \frac{1}{\rho(n) \cdot q \cdot \mu H(n)} \frac{\text{dopant atoms}}{\text{cm}^3}$$

where q is the electronic charge, $1.602 \times 10^{-19}$ coulombs.

For silicon doped with both acceptors and donors it is normally accepted that for p-type silicon, the concentration of holes p, is given by $N_A - N_D$, where $N_A$ is the concentration of acceptor atoms and $N_D$ is the concentration of donor atoms; and that for n-type silicon, the concentration of electrons, n, is given by $N_D - N_A$. For pn junctions, this relationship is accepted, except for the immediate region on both sides of the junction where the concentration of holes and electrons are controlled by space charge effects.

Since the resistivity is determined by the concentration of holes and electrons, the space charge effects can affect the resistivity and dopant concentration values in the immediate vicinity of the junctions.

Although the carrier distribution can be calculated from the dopant distribution, the inverse problem needs an assumption for the dopant distribution. We can use the Poisson-Boltzmann equation to calculate the corresponding carrier distribution. From this carrier distribution, we can calculate the sheet resistance value. Comparison of the measured sheet resistance with the calculated sheet resistance values permits us to adjust the assumed dopant distribution until we get a match between the measured and calculated sheet resistance values.

Examining our experimental data, we note that the sheet resistance increases monotonically with the distances $X_i$, $X_2$, ... $X_{n-1}$, $X_a$ from the original surface until it reaches an unstable value which we interpret as signifying that an electrical junction no longer exists.

Our approach is to begin with our last two significant sheet resistance values measured at $X_n$ and $X_{(n-1)}$, i.e. $R_{s(n)}$ and $R_{s(n-1)}$. We introduce two approximations, $X_j^M$, the junction depth, i.e. the distance from the original surface to the metallurgical junction, where $N_A = N_D$; and $m_{(n-1)}$ the linear impurity concentration gradient between $X_{(n-1)}$ and $X_j^M$. Thus $X_j^M - X_n$ represents the distance between the last significant measurement and the metallurgical junction. The other two values required for this calculation are known. These are $N_D$, the impurity concentration of the substrate, and ΔX, the distance between $X_n$ and $X_{(n-1)}$.

The program which applies the Poisson-Boltzmann equation and the two carrier equations shown below is referred to as a Poisson equation solver. In this method, the Poisson equation:

$$\nabla^2 \psi = -\frac{q}{\varepsilon_0 \kappa_3}(N_D - N_A + p - n) - \frac{q}{\varepsilon_0 k_2}(mx + (p-n)_x)$$

and the charge density equations $$n = n_i \exp\left(\frac{e\psi}{kT}\right) \text{ and } p = n_i \exp\left(-\frac{e\psi}{kT}\right)$$

are solved simultaneously. The boundary conditions on these calculations that we assumed are that the surface charge is constant and that the first derivative of the potential should be zero deep in the substrate.

The Poisson solver gives us the concentration distribution of the carriers, $p_x$ and $n_x$. This in turn permits us to obtain the net excess hole concentration $(p-n)_x$ and the position of the electrical junction, $X_j^E$ where $p_x = n_x$. We are now in a position to calculate the resistivity distribution, $\rho(x)$, over the distance $X_n$ to $X_j^E$, using an A.S.T.M. algorithm $$\rho(x) = \frac{1.305 \cdot 10^{16}}{(p-n)_x} + \frac{1.133 \cdot 10^7}{(p-n)_x[1 + 2.58 \cdot 10^{-19}(p-n)_x]^{-0.737}}$$

On the basis of estimations of $m_{(n-1)}$ and $X_j^M$, we can calculate $R'_{s(n)}$, the sheet resistance at $X_{(n)}$, as follows:

$$R'_{s(n)} = \left[\int_{x_n}^{x_j^E(n)} \frac{dx}{\rho(x)}\right]^{-1}$$

and compare it with $R_{s(n)}$, the sheet resistance measured at distance $X_n$ from the original surface. Using the identical estimation of $m_{(n-1)}$ and $X_j^M$ we can apply Poisson's equation over the interval from $X_{(n-1)}$ to $X_n$ and beyond. From these new carrier distributions, we can obtain $X_{j\,(n-1)}^E$ and $(p-n)_x$ and calculate $R'_{s(n-1)}$, the sheet resistance measured at $X_{(n-1)}$ $$R'_{s(n-1)} = \left[\int_{x_{(n-1)}}^{x_j^E(n-1)} \frac{dx}{\rho(x)}\right]^{-1}$$

We compare the calculated values of $R'_{s(n)}$ and $R'_{s(n-1)}$ with the corresponding measured values, $R_{s(n)}$ and $R_{s(n-1)}$. If they agree, we accept the estimated values of $m_{(n-1)}$ and $X_j^M$. If not, we iterate the values of $m_{(n-1)}$ and $X_j^M$ until we obtain a match for both $R_{s(n)}$ and $R_{s(n-1)}$ with their calculated values. Having established the values of $m_{(n-1)}$ and $X_j^M$, we can express the impurity distribution between $X_{n-1}$ and $X_j^M$ as $$(N_A-N_D)_x = m_{n-1}(X_j^m - X)$$

We now turn our attention to the segment between $X_{(n-2)}$ and $X_{(n-1)}$. Our calculation here is considerably simplified since we have only one variable to iterate, $m_{(n-2)}$, the linear dopant gradient between $X_{(n-2)}$ and $X_{(n-1)}$. Using the values of $m_{(n-1)}$ and $X_j^M$ obtained in our first calculation, we can iterate $m_{(n-2)}$ until we obtain a match between the measured sheet resistance at $X_{(n-2)}$, $R_{s(n-1)}$, and the value calculated for this point. This permits us to express the impurity distribution from $X_{(n-2)}$ to $X_{(n-1)}$ as $$(N_A-N_D)_x = m_{(n-1)}(X_j^M - X_{n-1}) + m_{(n-1)}(X_{n-1} - X)$$

We continue this process to the interval between $X_{n-3}$ and $X_{n-2}$. The total estimated impurity distribution now corresponds to $$N_A - N_D = m_{(n-1)}(X_j^M - X) \text{ for } X_j^M > X > X_{n-1}$$

$$N_A - N_D = m_{(n-1)}(X_j^M - X_{(n-1)}) + m_{(n-2)}(X_{(n-1)} - X) \text{ for } X_{n-1} > X > X_{n-2}$$

$$N_A - N_D = m_{(n-1)}(X_j^M X_{(n-1)}) + m_{(n-2)}(X_{(n-1)} - X_{(n-2)}) + m_{(n-3)}(X_{(n-2)} - X) \text{ for } X_{n-2} > X > X_{n-3}$$

Here we have already established values for $X_j^M$, $m_{(n-1)}$ and $m_{(n-2)}$ $X_n$, $X_{(n-1)}$, $X_{(n-2)}$, and $X_{(n-3)}$ are known distances from the original surface. The only variable we are estimating is $m_{(n-3)}$. As before we can iterate $m_{(n-3)}$ and calculate $R_{s(n-1)}$. This process can be continued only a few times before we pass out of the space charge region and reach a region where calculated $R_s$ = measured $R_s$.

The mathematical technique herein described can be incorporated into a computer program which will collect the electrical measurements, calculate a profile for the sheet resistance during the anodic oxidation run, estimate a series of m values and distances for the deepest segment of the impurity distribution, apply the Poisson-Boltzmann solver, calculate sheet resistance for each set of assumed m and distance values, and choose the values which result in calculated sheet resistivities which match the values obtained from the last two electrical measurements. Having established the impurity distribution for the last two segments, the program will then proceed to evaluate a few adjoining segments in turn.

A number of embodiments of the invention have been described. Nevertheless, it will be understood that various modifications may be made without departing from the spirit and scope of the invention. For example, a sequence of thin alternating type semiconductor layers can be evaluated layer by layer. The layers can also be III–IV semiconductors or other materials. The anodic oxidation can be assisted by focused light, e.g., for n type surfaces. Accordingly, other embodiments are within the scope of the following claims.

What is claimed is:

1. A method of determining the resistivity profile in a pn structure or in the silicon surface layer on a SOI (silicon on insulator) structure comprising the steps of:
   placing a substrate with a resistor test structure having a conduction circuit including a semiconductor layer on said pn or SOI structure at a measurement station;
   converting successively deeper sublayers of the semiconductor layer from the conduction circuit into a surface oxide by anodic oxidation at the measurement station;
   measuring a sheet resistance of the conduction circuit at the measurement station after converting each sublayer and without removing the surface oxide to generate a plurality of sheet resistance measurement; and
   calculating the resistivity profile from the plurality of sheet resistance measurements.

2. The method of claim 1, further comprising measuring an initial sheet resistance of the conduction circuit prior to converting any sublayers.

3. The method of claim 1, wherein measuring the sheet resistance is performed alternately with the anodic oxidation.

4. The method of claim 1, wherein anodic direct current is applied between a cathode and the test structure with a constant current source, and an incremental forming voltage is measured and used to determine a thickness of a converted sublayer.

5. The method of claim 1, wherein the anodic oxidation is confined to a small area where the test structure is located.

6. The method of claim 5, wherein the resistor test structure is a cross van der Pauw resistor, and wherein the anodic oxidation is confined to the intersection of the arms of the cross van der Pauw resistor.

7. The method of claim 6, wherein the resistance is measured by applying an alternating current through two arms of the van der Pauw resistor and measuring the voltage drop across the contacts on the opposite two arms.

8. The method of claim 1, wherein measuring the sheet resistance measurement is performed without removing an overlying electrolyte.

9. The method of claim 8, wherein anodic oxidation is paused during measuring the sheet resistance.

10. The method of claim 1, further comprising calculating a dopant concentration distribution of the pn structure or silicon surface layer from the resistivity profile.

11. The method of claim 10, wherein the dopant concentration distribution is calculated from the resistivity profile on the basis of specific mobility data.

12. The method of claim 10, wherein the dopant concentration distribution is calculated from the resistivity profile on the basis of A.S.T.M. Standard F723.

13. The method of claim 1, wherein converting sublayers of the conduction circuit is carried out non-destructively on a production wafer such that the production wafer can be returned to the production process.

14. The method of claim 1, further comprising applying a magnetic field to the resistor test structure and measuring Hall sheet coefficients.

15. The method of claim 14, further comprising calculating a mobility profile from the Hall sheet coefficients.

16. The method of claim 1, wherein the semiconductor layer of the resistor test structure is electrically isolated from a remainder of the semiconductor layer of the substrate.

17. The method of claim 1, wherein the semiconductor layer comprises a silicon substrate.

18. A method of processing a substrate, comprising:
   forming a test structure having an electrically isolated semiconductor layer at a substrate surface in a production integrated circuit substrate;
   receiving the substrate at a measurement station;
   converting successively deeper sublayers of the semiconductor layer from the surface of the semiconductor layer into a surface oxide by anodic oxidation at the measurement station;
   making a respective sheet resistance measurement of the semiconductor layer after converting each of the sublayers and without removing the surface oxide to provide a plurality of resistance measurements;
   calculating a resistivity profile for the semiconductor layer from the plurality of resistance measurements; and after making the plurality of resistance measurements, performing at least one additional processing step on the substrate in the fabrication of integrated circuits on the substrate.

19. A method of characterizing a semiconductor layer, comprising:
   receiving at a measurement station a substrate that includes a structure having an electrically isolated semiconductor layer at a substrate surface,
   successively oxidizing a plurality of successively deeper semiconductor sublayers from the surface of the semiconductor layer to provide a successively deeper oxide portion on the surface of the substrate;
   making a respective sheet resistance measurement of the semiconductor layer after the oxidation of each of the plurality of sublayers without removing the oxide portion and while the oxidized portion is on the surface of the substrate to provide a plurality of resistance measurements, and calculating a resistivity profile for the semiconductor layer from the plurality of resistance measurements.

20. The method of claim 19, wherein converting the sublayer of the substrate into the oxide portion includes:
   positioning a receptacle over a test region of substrate including the structure, the receptacle defining an opening to the test region within a limited area;
   adding an electrolyte into the receptacle positioned over the test region, the electrolyte contacting the test region in the limited area; and
   applying an electric current through the electrolyte and the substrate.

21. The method of claim 20, wherein:
   positioning the receptacle over the test region includes placing a seal between the substrate and the opening of the receptacle, the seal confining the electrolyte to the test region.

22. The method of claim 20, wherein the electrolyte includes an aqueous solution.

23. The method of claim 20, wherein the electrolyte includes a non-aqueous solution.

24. The method of claim 20, wherein:
   the test region includes a cross of a van der Pauw resistor.

25. The method of claim 24, wherein a test structure includes the central portion and four elongated arms attached to the central portion, and wherein:
   measuring the sheet resistance in the test region includes passing a test current through two adjacent arms of the test structure and measuring voltage across two of the remaining arms of the test structure.

26. The method of claim 25, wherein the test current includes an alternating current.

27. The method of claim 19, wherein:
   measuring the sheet resistance includes measuring a sequence of values for the sheet resistance, each value measured for the sheet resistance at a different depth of the oxide portion.

28. The method of claim 27, further comprising:
   determining a respective depth of the oxide portion for each value measured for the sheet resistance.

29. The method of claim 28, wherein:
   converting the layer of the substrate into the oxide portion includes applying a predetermined electric current between a cathode and the substrate; and
   determining the depth of the oxide portion includes determining the depth of the oxide portion based on a voltage drop between the cathode and the substrate.

30. The method of claim 28, further comprising:
   determining one or more values of a differential resistivity based on two or more of the values measured for the sheet resistance, each value of the differential resistivity being determined for a respective depth in the substrate.

31. The method of claim 30, further comprising:
   estimating a dopant distribution in the substrate based on the determined values of the differential resistivity.

32. The method of claim 19, wherein:
   measuring the sheet resistance includes suspending the conversion of the semiconductor layer of the substrate into oxide while the sheet resistance is measured.

33. The method of claim 19, further comprising applying a magnetic field to the test region and measuring a Hall sheet coefficient.

34. The method of claim 33, further comprising applying a positive magnetic field to the test region and measuring a first Hall sheet coefficient and applying a negative magnetic field to the test region and measuring a second Hall sheet coefficient.

35. The method of claim 33, wherein:
   measuring the Hall sheet coefficient includes measuring a sequence of values for the Hall sheet coefficient, each value measured for the Hall sheet coefficient at a different depth of the oxide portion.

36. A system for characterizing layers in semiconductor substrates, the system comprising:
   a receptacle configured to receive an electrolyte and confine the received electrolyte to contact a surface of a semiconductor substrate in a limited test region;
   a cathode configured to make electrical contact with the electrolyte in the receptacle;
   an anodic current generator configured to pass an electric current through the cathode and the electrolyte to the substrate to successively convert deeper sublayers of a layer of the substrate into an anodic oxide layer in the test region; and
   a sheet resistance meter configured to measure sheet resistance after the conversion of each of the sublayers without removing anodic oxide layer in the test region while the anodic oxide layer is on the substrate.

37. The system of claim 36, further comprising:
   a controller to control the anodic current generator or the sheet resistance meter.

38. The system of claim 36, further comprising:
   a first voltage meter configured to measure a voltage drop between the cathode and the substrate.

39. The system of claim 36, wherein the sheet resistance meter is configured to make electric contacts with four contact points arranged around a singly connected region of a test structure in the test region.

40. The system of claim 39, wherein the sheet resistance meter includes:
   a test current generator to pass a test current through two adjacent contact points of the test structure; and
   a second voltage meter to measure voltage across two of the remaining contact points of the test structure.

41. The system of claim 40, further comprising a magnet to apply a magnetic field to the test region.

42. The system of claim 41, wherein the sheet resistance meter is configured to measure a Hall sheet coefficient.

43. The system of claim 36, further comprising a controller configured to calculate a resistivity profile from the plurality of sheet resistance measurements.

* * * * *

UNITED STATES PATENT AND TRADEMARK OFFICE
CERTIFICATE OF CORRECTION

PATENT NO. : 7,078,919 B2  Page 1 of 1
APPLICATION NO. : 10/927945
DATED : July 18, 2006
INVENTOR(S) : Simon A. Prussin It is certified that error appears in the above-identified patent and that said Letters Patent is hereby corrected as shown below:

Col. 21, claim 19, line 13, change "oxidized" to --oxide--.

Col. 22, claim 36, line 15, after "removing" insert --the--.

Signed and Sealed this

Twenty-seventh Day of March, 2007

JON W. DUDAS
*Director of the United States Patent and Trademark Office*